US006438279B1

(12) United States Patent
Craighead et al.

(10) Patent No.: US 6,438,279 B1
(45) Date of Patent: Aug. 20, 2002

(54) UNITARY MICROCAPILIARY AND WAVEGUIDE STRUCTURE AND METHOD OF FABRICATION

(75) Inventors: Harold G. Craighead; Mathieu E. Foquet; Warren Wright, all of Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/448,413

(22) Filed: Nov. 23, 1999

Related U.S. Application Data

(60) Provisional application No. 60/115,137, filed on Jan. 7, 1999.

(51) Int. Cl.[7] ................................................. G02B 6/10
(52) U.S. Cl. ......................... 385/12; 385/37; 385/130; 385/16; 356/246
(58) Field of Search ........................... 385/12, 37, 130, 385/131, 14, 15, 16; 356/244, 246

(56) References Cited

U.S. PATENT DOCUMENTS

| 5,094,517 A | * | 3/1992 | Franke | 385/12 |
| 5,173,747 A | | 12/1992 | Boiarski et al. | 385/12 X |
| 5,192,502 A | | 3/1993 | Attridge et al. | 385/12 X |
| 5,430,541 A | | 7/1995 | Sapp et al. | 356/246 |
| 5,439,647 A | | 8/1995 | Saini | 385/12 X |
| 5,446,534 A | | 8/1995 | Goldman | 385/130 X |
| 5,867,266 A | | 2/1999 | Craighead | 356/246 |

* cited by examiner

*Primary Examiner*—Phan T. H. Palmer
(74) *Attorney, Agent, or Firm*—Schwegman, Lundberg, Woessner & Kluth, P.A.

(57) ABSTRACT

Fabrication techniques for forming arbitrarily shaped fluid capillaries at dimensions below 1 μm and for forming optical waveguides in the same devices with the same fabrication processes include methods to make integral optical waveguide/fluid-flow systems for greater miniaturization, integration and parallelism of optical excitation and detection systems for the sampling of small volumes. Capillaries with widths below 1 μm dimensions are fabricated using photolithography and reactive ion etching on glass substrates or by provision of a sacrificial layer, having the configuration desired for a microchannel, covered by a high refractive index material in which a waveguide is formed. Removal of the sacrificial layer produces a microchannel aligned with the waveguide. Dye labeled DNA molecules are driven electrophoretically through the micrometer size channels light emission from and individual molecules can be observed.

22 Claims, 10 Drawing Sheets

Schematic of the capillary/Waveguide structure.

FIG. 1
Schematic of the capillary/Waveguide structure.

FIG. 2
PLAN VIEW

FIG. 3
SIDE VIEW

FIG. 11 Computer design of central fluid/waveguide area

FIG. 12 Scanning electron micrograph (SEM) of fabricated device in Silica

FIG. 13 Scanning electronmicrograph with interaction region expanded

FIG. 14 SEM with sample tilted to show perspective and side walls

FIG. 16

SEM image of a small portion of the grating coupler showing the 500nm period grating.

FIG. 15

SEM image of a finished sample showing the interaction region.

UNITARY MICROCAPILLARY AND WAVEGUIDE STRUCTURE AND METHOD OF FABRICATION

This application claims the benefit of provisional application 60/115,137, filed Jan. 7, 1999 and entitled "Fluorescence Spectrometer for Femtoliter Volumes", the disclosure which is hereby incorporated herein by reference.

The present invention was made with Government support under Grant No. 1 R21 HG 01519 awarded by the National Institutes of Health. The Government has certain rights in the invention.

BACKGROUND OF THE INVENTION

The present invention relates to techniques for fabricating fluid microcapillaries and optical waveguides in a single device using the same fabrication process, and to optical/fluid flow systems for miniaturized optical excitation and detection devices for use in optical sampling of small volumes of fluid.

Fluorescence is one of the main tools biologists and biochemists have used to understand the processes of life. It is routinely used in laboratories to monitor the progress of biochemical reactions in vitro or in vivo, to measure the produced, consumed, and available quantity of important biological agents, such as proteins or DNA, and to study the dynamics of living cells at a molecular scale. Fluorescence has several advantages as a probe for biochemical processes. Extremely small amounts of dye can yield a large signal, minimizing the perturbation of the natural process. Some dyes exhibit drastic changes in fluorescence quantum yield or in emission spectrum on binding, giving a high specificity of the signal on the environment. Furthermore, it is more available and practical than radioactive markers. Finally, improvements in detection apparatus have shown that fluorescence can reach the highest sensitivity possible; namely, temporally resolved single molecule detection.

The optics available for use in the detection of low level light emissions, such as fluorescence, phosphorescence, chemoluminescence, Raman scattering, etc., which will hereafter be referred to generally as fluorescence, the use of lasers as light sources, and detection methods like confocal microscopy and two-photon excitation have pushed detector probe volumes to lower and lower sizes. Such small probe volumes have provided a higher sensitivity for the detectors, due the decrease in the Raman background from the solvent. These detectors have also brought a wealth of new information on the dynamics of measurement systems through the study of the signal correlation functions. In parallel to that evolution, the amount of re-agent that biochemists have used for their experiments has been decreasing steadily. Smaller and smaller liquid handling systems are now being fabricated to handle the new needs.

Ultimately, processes and methods from the semiconductor industry are used to create the evolved structures necessary to control the small amounts of fluid. However, the techniques used for the detection process have not followed the same path. Since efficient single-fluorophore detection and analysis could lead to significant new applications in analytical chemistry and biology, improved devices and methods of fabricating such devices are needed.

SUMMARY OF THE INVENTION

It is an object of the present invention to provide an improved apparatus for efficiently collecting light emitted from femtoliter volumes of fluids.

It is another object of the invention to provide a device for delivering laser radiation to femtoliter volumes of fluid in order to efficiently excite light emission, and to provide a unique method for fabricating such a device.

It is another object of the invention to provide a new integrated device for performing optical detection and spectroscopy of a single light-emitting molecule in a highly confined, flowing fluid and, more particularly, to detect target materials such as single molecules or single cells in a very small volume.

It is another object of the invention to provide a device for delivering laser radiation to a small volume of fluid in order to efficiently excite light emission from target materials, by integrating a fluid flow channel with an optical waveguide and by providing for light collection optics for such a device.

It is still another object of the invention to create a significant new apparatus for rapid, continuous flow sequencing of single DNA fragments by efficiently identifying fluorescently labeled bases in a flowing liquid.

A still further object of the invention is to provide a method for fabricating a unitary microcapillary and optical waveguide device for use in single molecule detection.

Briefly, in accordance with the present invention, an integrated fluid channel and optical waveguide is fabricated by simultaneously microfabricating one or more microchannels for the flow of fluids and one or more optical waveguides for providing illumination of such channels. The fabrication process provides miniaturization, integration and parallelism of optical excitation and detection devices for the sampling of various small volumes of fluids by providing at least one submicrometer channel; i.e., a fluid channel preferably having a width smaller than one micrometer and a depth of between about 0.125 $\mu$m and about 1.0 $\mu$m, depending on the material being monitored, and at least one intersecting optical waveguide. In one embodiment, both the microchannel and the waveguide are fabricated simultaneously on a common substrate using, for example, photolithography and reactive ion etching in dielectric layers on glass or on silicon substrates. The submicrometer fluid channel will be referred to herein as a microchannel or microcapillary. In use, target materials such as dye-labeled molecules may be electrophoretically driven through the microchannel while laser light is coupled into the waveguide which intersects it, to excite the dye and to produce emitted light. An optical detector permits observation of the light emitted from individual molecules.

The dimensions of the microchannel and the waveguide provide a small, well-defined interaction volume in the channel, resulting in a lower probability of having more than one target element such as a molecule in the interaction volume and providing decreased background noise. The small portion of the microchannel structure subjected to the excitation light reduces background light and increases the efficiency of the detection process. Although the detection of single fluorophore molecules is a primary objective, similar structures can also be used to study other materials, such as polymer strands, in restricted channels, leading to a better understanding of the electrophoresis phenomenon, for example.

The present invention provides several new devices and techniques for improving the optics and fluid flow control in a monitoring or inspection device, and these are particularly useful, for example, in improving the delivery of laser excitation to fluorescently labeled molecules such as DNA nucleotides. The optical waveguide which is integrated into the same structure as the microchannel structure accurately and reliably aligns the laser with the microchannel, and limits the laser excitation to a very small interaction volume, for the waveguide confines the laser beam to a small, well-defined, propagation path. The structure is capable of providing extremely small interaction volumes, in the sub-femtoliter range, and thus is suitable for the detection of extremely small quantities of fluorophores. Beam confinement in the waveguide is similar to confinement in silica optical fibers, although in the disclosed embodiment, a rectangular waveguide is used. Although the invention is described herein with a single fluid microchannel intersecting a single waveguide, it will be understood that, if desired, multiple, parallel, spaced microchannels may be provided, with a single waveguide intersecting all of them, so that light passes through the respective interaction regions in sequence. In addition, multiple parallel waveguides may be provided to intersect a single microchannel or to intersect multiple parallel microchannels.

In one embodiment of the invention, one or more microchannels are fabricated on glass or silicon substrates with minimum channel widths of about 1.0 micrometers for glass or 0.6 micrometers for silicon. Glass-based substrates may include a variety of materials, such as Pyrex, Corning Borofloat, UV grade fused silica, and microscope coverslips. In each case, the substrates are thoroughly cleaned as a first step, and are then covered with a 1.0 micrometer thick layer of doped silicon oxide, preferably deposited by PECVD. This yields a layer of nonstoichiometric silicon oxide, with an index of refraction of around 1.51, which forms a dielectric layer in which one or more microchannels and one or more integral waveguide structures are to be fabricated. The resulting wafers, or samples, are then covered with an opaque layer, such as an aluminum film, which is to be used as an etch mask. At least one waveguide and one or more microchannels of desired shape and width are then exposed in a resist layer, and the resist pattern is transferred to the mask layer in conventional manner. The dioxide layer is then dry etched through the mask pattern in a $CF_4/O_2$ plasma to transfer the microchannel and waveguide patterns, and the mask layer is then removed.

Glass-based microchannels are covered with a microscope coverslip coated, for example, by spinning, with a thin layer of poly-dimethylsiloxane (PDMS) polymer. Since PDMS is hydrophobic in its natural state, a short oxygen plasma treatment is used to modify this characteristic. The coverslip is then placed in contact with the patterned dioxide layer on the substrate, and bonding spontaneously occurs.

The waveguide for illuminating the microchannel is fabricated using the same photolithography and etching steps that are used for fabricating the microchannel. Channels are etched in the one micrometer thick layer of nonstoichiometric silicon oxide on each side of the waveguide to form a ridge which is used as the waveguide. To compensate for the presence of defects in the oxide layer, a beam-coupling region of the waveguide, which receives illuminating light from a suitable source, is fabricated to have a width of 100 micrometers. However, the waveguide preferably narrows down as it approaches the microchannel, with the rate of narrowing being slow enough to convert the energy of the laser light from the fundamental mode of the wide waveguide to the fundamental mode of the narrow waveguide. The laser light may be coupled directly into the wide end of the ridge waveguide, or in the alternative, a grating may be fabricated lithographically at the large end of the waveguide to facilitate coupling. The grating may be produced by covering the sample with a resist layer and exposing the resist through a pattern using e-beam lithography. The resist is developed and 100 nanometers of the silicon oxide dielectric forming the ridge are etched through the pattern, using conventional reactive ion etching (RIE).

The foregoing fabrication procedures permit simultaneous formation of submicron fluid channels and automatically aligned ridge waveguides in a single integral photolithographic and etching process. The process allows the waveguide to have a cross sectional area as small as one micrometer at the region where it approaches the microchannel, thereby providing a femtoliter interaction region in the corresponding fluid channel. For single molecule detection, as well as for the detection of small numbers of molecules, signal-to-noise ratios are vastly improved, since the effective density of fluorophores in the fluid channel is vastly increased.

An alternative, and preferred, process for fabricating an integral microchannel and optical waveguide device includes formation of a sacrificial layer which is shaped to define the desired microchannel configuration on a substrate such as fused quartz. A high refractive index layer of a material such as doped silicon dioxide is then deposited on the top surface of the substrate, covering the shaped sacrificial layer. Conventional lithographic and etching processes are then used to fabricate a ridge waveguide by etching channels in the silicon dioxide layer, and to etch irrigation holes through the silicon dioxide layer to expose the sacrificial layer. A grating may then be etched on the top surface of the ridge waveguide, as previously described, and the sacrificial layer is removed, using wet chemistry supplied through the irrigation holes. Thereafter, the irrigation holes are covered to close the fluid channel and, if desired, the channels defining the ridge waveguide may be filled by depositing a material having a low index of refraction. Thereafter, access wells may be etched through the covering material to provide access to the microchannel.

The fabrication of integral microchannel and waveguide structures utilizing the foregoing microlithographic techniques on the same substrate to form an integrated unit provides the foregoing structures at a low cost. Furthermore, multiple microchannel systems fed by one or more cross-connecting, single-mode waveguides can be readily fabricated.

Large angle collection optics can be integrated into the microcapillary-waveguide structure of the present invention, thereby enabling geometrical collection efficiencies of up to 80%. Furthermore, since the laser beam path is completely separated from the detection system optics, laser scattering from optical surfaces in the detection system is avoided. Because the present device reduces scattering noise and increases collection efficiency, a continuous wave excitation laser can be employed, and such a laser is less complex and less expensive than a pulsed laser/gated detection system.

The present device is extremely versatile, providing multimode optical waveguides and capillaries fabricated with dimensions on the order of tens of microns.

BRIEF DESCRIPTION OF THE DRAWINGS

The foregoing, and additional objects, features advantages of the present invention will be apparent to those of skill in the art from the following detailed description of preferred embodiments thereof, taken in conjunction with the accompanying drawings, in which.

DESCRIPTION OF PREFERRED EMBODIMENTS

Figure 1:
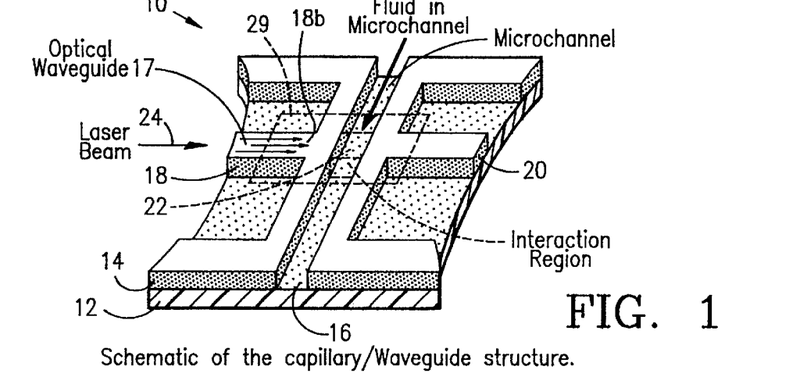
FIG. 1 is a diagrammatic, perspective view of a microcapillary/optical waveguide device fabricated in accordance with the present invention.

Turning now to a more detailed description of the present invention, FIG. 1 illustrates in diagrammatic perspective view an integrated flow channel/optical waveguide device which is suitable for optical inspection of fluids or other materials in the flow channel. Although the device of the present invention is particularly suitable for single molecule detection of DNA tagged with fluorophores, it is also suitable for inspection of a wide variety of target materials in a minimal scattering, femtoliter fluid flow channel interaction volume. An integral waveguide delivers laser excitation from a suitable source, which may be a continuous wave (CW) laser, to the interaction volume to produce light emissions, such as laser-induced fluorescence (LIF), in the fluid in the channel. The integrated flow channel/optical waveguide device in accordance with the present invention is illustrated generally at 10 in FIG. 1. The illustrated device may be fabricated on a glass or silicon substrate 12 on which is formed an oxide layer 14 which may be silicon dioxide (silica), germanium dioxide (germania) or the like. A microchannel 16 is fabricated in layer 14 by a photolithographic and dry etch process to be described. The same process is used simultaneously to fabricate an integral optical waveguide 17 having input and output optical waveguide segments 18 and 20, respectively, in the oxide layer 14 to produce the device 10 on a single chip, or wafer. In accordance with a preferred form of the invention, the waveguide and the fluid channel intersect each other, and both have cross sectional areas of about one square micrometer, or less, at an interaction region 22 where they intersect.

The waveguide segments 18 and 20 are aligned with each other along a first, common axis while the microchannel 16 lies on a second axis passing through the axis of the waveguide, with the two axes preferably being perpendicular to each other. The waveguide and the microchannel intersect at the interaction region 22, which may also be referred to as a scattering volume, where light from a laser beam 24 propagating through the input waveguide segment 18 illuminates fluids flowing in the microchannel 16. The beam illuminates a small and well-defined region 22, with the light passing through fluid in the channel and exiting the interaction region through the outlet waveguide segment 20. Although not illustrated, it will be understood that the light in waveguide segment 20 may be directed to a second microchannel substantially parallel to and spaced from microchannel 16 on the substrate 12 for illuminating fluid in the second, or parallel, microchannel, and may similarly be directed to additional such channels, in sequence, so that a single laser source may illuminate multiple parallel channels. It will also be understood that additional waveguides may be provided in parallel to waveguide 17 to intersect microchannel 16 and additional microchannels parallel thereto. The microchannel 16 carries a material to be studied under the laser light. For example, this material may be an aqueous solution including dye-labeled DNA molecules which may be driven electrophoretically through the micrometer-sized channel 16. Surface energy on the relatively high surface area microchannel 16 assists in filling the microchannel with the solution, and the liquid-contacting surfaces of the microchannel may be treated to facilitate flow. In this example, the light beam 24 induces fluorescence in the dye carried by the DNA molecules, and because of the small size of the interaction region 22, fluorescence induced in a single molecule may be detected.

Figure 2:
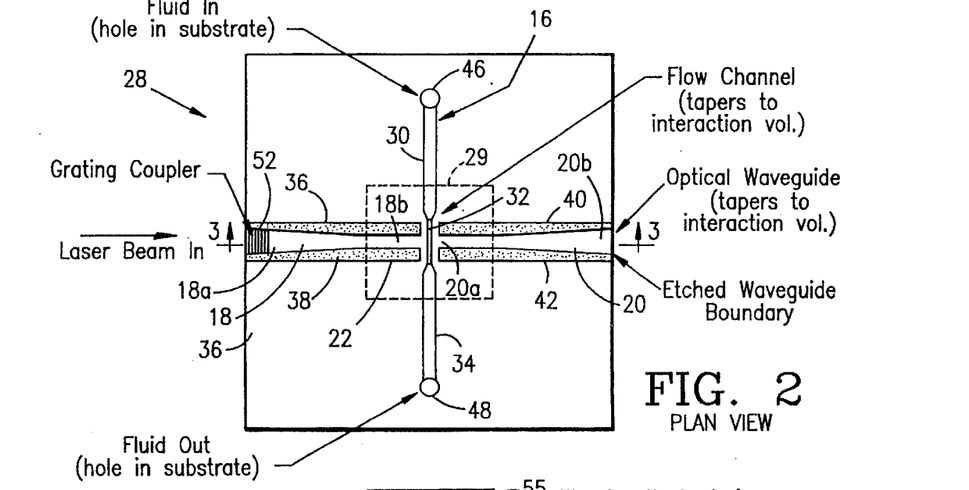
FIG. 2 is a diagrammatic top plan view of microcapillary/optical waveguide device in accordance with the invention.
Figure 3:
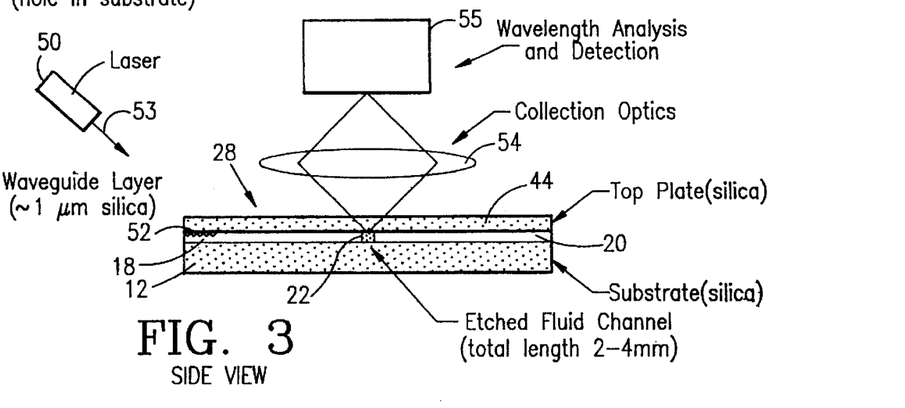
FIG. 3 is a cross sectional view of the device of FIG. 2, taken along lines 3—3 of FIG. 2.
Figure 4:
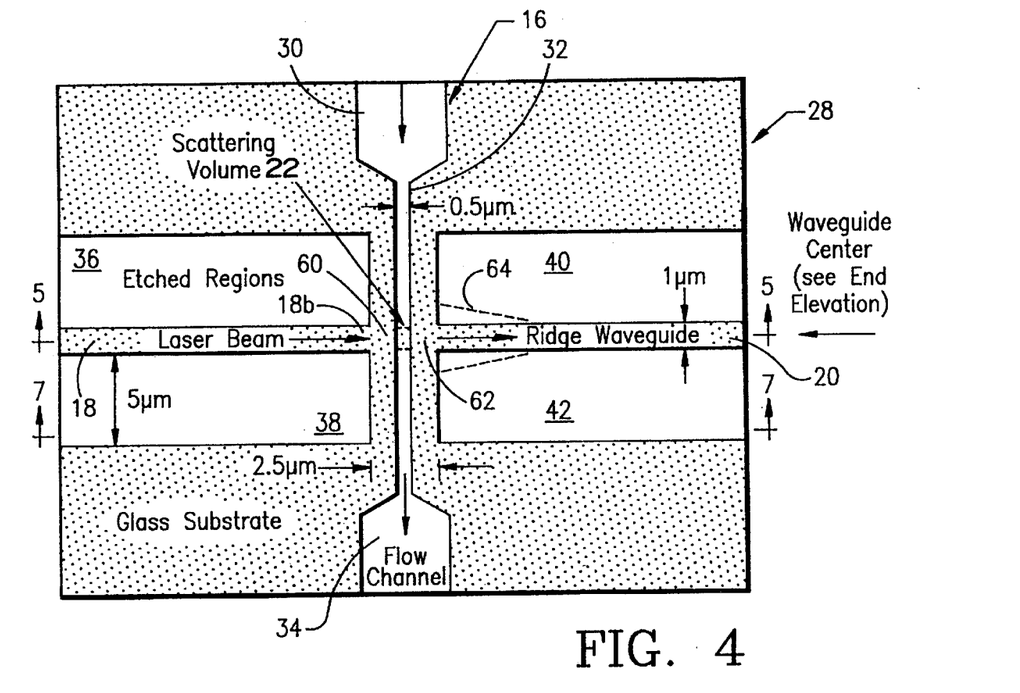
FIG. 4 is an enlarged, diagrammatic illustration of a portion of the device of FIG. 2.
Figure 5:
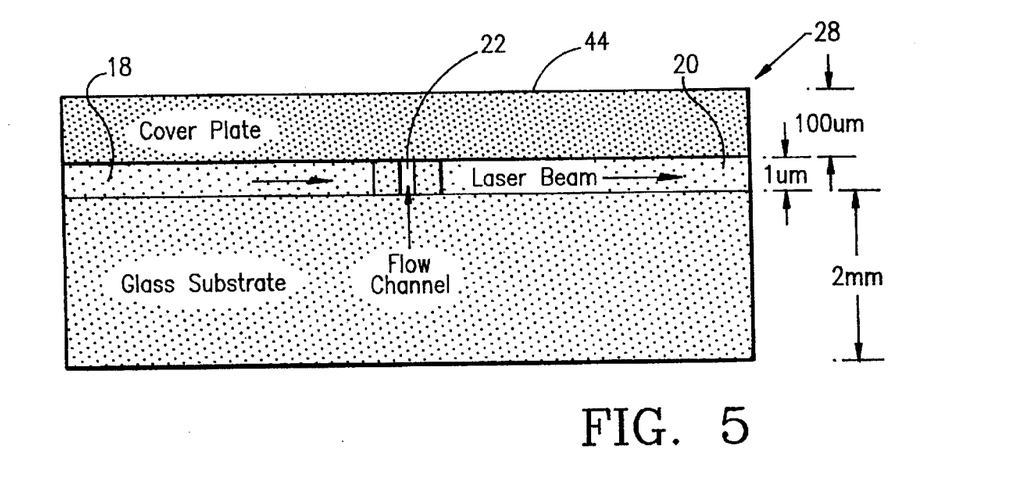
FIG. 5 is a cross sectional view taken along lines 5—5 of FIG. 4.

A more schematic illustration of an integrated flow microchannel and waveguide device is shown at 28 in FIGS. 2 and 3, and in the enlarged views of FIGS. 4 and 5. These figures illustrate a device 28 which is suitable for single molecule detection of DNA tagged with fluorophores as described above, with FIG. 2 illustrating the device in top plan view and FIG. 3 illustrating a cross-section taken along lines 3—3 of FIG. 2, with elements similar to those of FIG. 1 being similarly numbered. FIG. 4 is an enlargement of the area of intersection 29 surrounding the interaction region 22 of the microchannel and optical waveguide of FIG. 2, while FIG. 5 is an enlargement of the same region illustrated in FIG. 3.

As illustrated in these figures, a glass or silicon substrate 12 carries a layer 14 of oxide in which the microchannel or microcapillary 22 and the waveguide segments 18 and 20 are simultaneously fabricated. The microchannel preferably is etched so as have a relatively wide region 30, to facilitate entry of fluid, which tapers inwardly to a narrow region 32 before its intersection with the optical waveguide at interaction region 22. Thereafter, the microchannel tapers outwardly to a relatively wide outlet region 34 to facilitate removal of the fluid.

The waveguide segments 18 and 20 preferably are fabricated by etching channels 36 and 38 in layer 14 on opposite sides of waveguide segment 18 and by etching channels 40 and 42 on each side of waveguide segment 20, leaving ridges of oxide, which form the waveguide segments, aligned with each other along an optical axis which passes through the interaction region 22 of the microchannel 16. The etched channels on each side of the ridge waveguide segments provide strong lateral confinement of light in the resulting waveguide 17. Critical alignment of the microchannel 16, which confines the fluid volume, with the waveguide, which confines the laser beam, is guaranteed in this embodiment by fabricating monolithically both the ridge waveguide and the microchannels integrally, in layer 14, with simultaneous processing.

The top of microchannel 16 and the top of waveguide segments 18 and 20 are covered by a transparent top plate 44 to close the microchannel and to provide a top surface boundary for the waveguide. The top surface of layer 14 forms the bottom of microchannel 16, and provides a bottom surface boundary for the waveguide. The top surface of layer 14 and the bottom of the cover plate are optically flat so that the cover can be optically contacted to and bonded to the layer 14 to seal the microchannel. Fluid access to the microchannel may be by way of inlet and outlet holes 46 and 48 extending through the substrate 12 or the cover 44 and intersecting opposite ends of the microchannel 16. These holes may be one millimeter in diameter, for example, and may be drilled ultrasonically through the bottom of the substrate, with capillary tubes connected to the holes to supply and to remove the fluid to be analyzed.

In order to facilitate coupling of a laser beam from an external laser 50 through free space into the input waveguide segment 18, the top surface of the inlet end 18a of segment 18 preferably is patterned and etched to provide a coupler grating 52. Light 53 from source 50 is directed onto grating 52 and a portion of the light is deflected into and along the axis of the waveguide in the form of propagating beam 24. Alternatively, the the external laser beam 24 may be directed axially into the waveguide, as by way of an optical fiber (not shown). Another option is to fabricate a laser diode on the substrate adjacent to the inlet end 18a of the waveguide to emit light directly into the waveguide.

Preferably, the inlet end of the waveguide is relatively wide, and may have a width on the order of 10 μm or more, to ensure maximum coupling with the light from source 50. The inlet waveguide segment 18 is tapered inwardly from the grating at coupler end 18a to a point near the area of intersection 29 so that the waveguide is narrow at outlet end 18b. Similarly, the output waveguide segment 20 is tapered outwardly from its inlet end 20a to its outlet end 20b, in the preferred form of the invention.

In the preferred form of the invention, the fluid microchannel is generally rectangular in cross section, with its depth being in the range of about 0.1 μm to 1.0 μm and its width being in the range of about 0.5 μm to 1.0 μm. The smallest dimension of the outlet end 18b of waveguide 18 is about 1 micrometer, this dimension being limited by the wavelength cutoff of light in the waveguide material. The resulting interaction volume 22 in the fluid carried by the microchannel may be approximately $0.5 \times 10^{-15}$ liter. When dye-labeled DNA molecules, for example, are driven electrophoretically through the microchannel 16 and are illuminated by the laser light from the waveguide 17 in this region, the light induces fluorescence in the dye. The small interaction region results in an increased probability of having only a single molecule illuminated by the laser light, thus increasing the probability of viewing fluorescence from a single molecule. The background noise and light scattering is reduced by providing such a small interaction region (or scattering volume), leading to an increased efficiency in detecting the molecules.

The fluorescence induced by the input laser light beam 24 may be detected through the transparent cover 44 by suitable optics, illustrated at 54 in FIG. 3. The light so detected is directed by optics 54 to conventional wavelength analysis and detection equipment 55. The axes of the laser beam waveguide and the microchannel, and the optic axis of lens 54 preferably are orthogonal, intersecting at the interaction region 22.

For fluid flows in the extremely small capillaries utilized in the present invention, turbulence and conductance need to be considered. For a cylindrical capillary with incompressible, viscous flow and parameters appropriate to the herein-described system, the Reynolds number is approximately $$R = \rho D v / \mu$$
$$= 2 \times 10^{-3}$$

where
 $D = 2$ μm, capillary diameter,
 $\rho = 1 \times 10^3$ Kg/m$^2$, density of water,
 $v = 1$ mm/s, fluid velocity,
 $\mu = 1 \times 10^{-3}$ Ns/m$^2$, viscosity of water,
which is much less than the turbulence boundary limit at $R = 2,000$. Hence the flow in the microchannel will always be laminar. From the Hagen-Poiseuille equation the pressure difference required to drive this flow in a capillary section of length, $L = 100$ μm passing through the scattering volume is $$\Delta p = 32 \mu L v / D^2$$
$$= 800 \text{ Pa}$$

which is a modest requirement. The capillary 16 preferably is ~1 μm deep and in the vicinity of the scattering volume it tapers down to widths in the range of less than 1 μm to about 10 μm. These estimations indicate that turbulence and frictional forces will not present problems in the present system.

To reduce its flow resistance, it is possible to deepen the flow channel in regions away from the interaction region by chemical etching. Even with no deepening of the channels, gravity-created pressures are sufficient to generate the pressure head to force the liquid through the channel.

The waveguide segments 18, 20, which are formed from the dielectric material 14, have a given refractive index (the core) and are surrounded by dielectric material of lower refractive index (the cladding). The waveguide structure of the herein-described embodiment is a ridge waveguide configuration which has a high n core (the ridge) in which most of the energy of the propagating light wave is confined. The cladding is the substrate 12 and cover plate 44, which consists of low n material confining the wave in the vertical direction, and the core-air interface provided by the etched regions 36, 38 and 40, 42, which confine the wave in the horizontal direction. The transverse dimensions of the waveguide determine the number of modes of propagation the waveguide can support, with single mode operation being achieved when the guide diameter is approximately equal to the cut-off wavelength.

To assess the feasibility, on purely physical grounds, of using a dielectric waveguide to deliver laser energy to the scattering volume, the basic propagation characteristics in all sections of the capillary-waveguide structure have been calculated. Consider a waveguide geometry with transverse dimensions as follows:

guide height, h=1 μm; guide width, w=1 μm.

This geometry is specifically for a single molecule scattering system and will receive detailed consideration, although other dimensions may be utilized for other scattering systems.

The refractive indices of the components of the structure at the laser wavelength (488 nm or 514 nm) used for modeling are:

| Core film layer - | $SiO_2/GeO_2$ - | n = 1.493 |
| Substrate - | fused silica - | n = 1.463 |
| Ridge waveguide sides - | air - | n = 1.000 |
| Cover plate - | fused silica - | n = 1.463 |

The $SiO_2/GeO_2$ (silica/germania) index was produced by a sol-gel technique. Sol-gel technology seems to offer the best optical performance in the visible region and is available commercially from Photonic Integration Research, Inc., which provides silica/germania glass waveguide layers on quartz. The literature also shows $SiO_2/TiO_2$ as a higher index sol-gel layer, and this material is an alternate choice. Because of the multiple sources and processes available for silica/germania the following calculations are for this material and index.

(a) Beam entrance and Exit

Consider firstly, beam exit into free space from the end of a single mode waveguide to be captured by a suitable microscope objective. The guide has a core index of refraction, n, and radius, a=0.5 μm, and for simplicity a Gaussian intensity profile characterized by a beam waist, (or 1/e intensity radius), $\omega_0$ is assumed. After propagating a distance, z, the beam radius, $\omega_1$, is given by $$\omega_1=\omega_0[1+(Z/Z_R)^2]^{1/2}$$

where $z_R=\pi\omega_0^2/\lambda$, is the Rayleigh length.

For $\omega_0=0.5$ μm, ($2\omega_0$=beam diameter=core diameter= $2a=1$ μm) and $\lambda=0.5$ μm and z=140 μm (objective working distance) the beam diameter at the lens is $$2\omega_1=2\times89\times\omega_0=89 \text{ μm}$$

which is sufficiently small to be captured by a suitable objective lens.

The reflectance of the beam back into the guide due to the core-free space interface is small and given by $$R=[(n-1)/(n+1)]^2=0.036$$

for n=1.47, typical for the waveguides herein described. Thus, the beam exiting from the waveguide can be readily captured by a microscope objective.

By reciprocity, the same technique can be used to introduce a single mode ($TEM_{00}$) laser beam into the guide through the side of the waveguide-capillary structure with high efficiency. As described above, the exciting laser beam is coupled into the end of the waveguide by a grating coupler etched into the waveguide surface.

(b) Beam Propagation within the Waveguide

The ridge waveguide structure described herein consists of a rectangular core, in which most of the energy of a laser light wave propagates, surrounded by dielectrics (the cladding) consisting of, at the sides: air, at the bottom: fused silica (the substrate), and at the top: fused silica (cover plate). Beam confinement and guided mode propagation occur for core-cladding differences in refractive index as small as Δn=0.003 and confinement is stronger as this difference increases.

Single mode, $TE_{00}$, propagation only is considered here, for the characteristics of the $TM_{00}$ mode are very similar. For the air-core interface at the sides of the guide:

$$\Delta n=1.493-1.000=0.493$$

and the effective refractive index, N, which determines the phase velocity is $$N=1.476$$

From the slab waveguide model, 99.6% of the wave energy is in the core dielectric so confinement is virtually total in the horizontal plane. For the core-cladding interfaces at the top and bottom of the guide:

$$\Delta n=1.493-1.463=0.03$$

and $$N=1.485$$

From the slab waveguide model, 93.5% of the wave energy is in the core dielectric so the beam is well confined in the vertical plane.

A more accurate modeling procedure uses the method of field shadows. From this model the effective refractive index of the guide, N, is obtained:

$$N=1.468$$

and the power confinement to the core is 79%. This model also predicts the cutoff conditions for higher order modes with the result that only the lowest order modes ($TE_{00}$ and $TM_{00}$) are below cutoff in the waveguide. These modes have a sinusoidal field distribution across the guide with a centered peak and no nodes. (In practice the profile may be a Gaussian or similar profile). This is desirable spatial distribution to have in the scattering volume to ensure uniform irradiation of fluorophores.

(c) Beam Propagation Through the Scattering Volume

The laser beam 24 traverses three short sections of total length 2.5 μm between leaving the ridge waveguide 18 on the left hand side (LHS) (FIG. 4) and entering the ridge waveguide 20 on the right hand side (RHS). As the beam 24 approaches the scattering volume 22 (FIG. 4) it exits the ridge waveguide and propagates a short distance (~1 μm) through the region 60 of the dielectric layer 14 to the left side of the scattering volume. In this region 60 the beam 24 is propagating in a slab waveguide with confinement in the vertical direction due to the lower index substrate and cover plate. As calculated above, using the slab waveguide model, 93.5% of the beam energy is confined to the core region (the 1 μm $SiO_2$—$GeO_2$ film 14). The beam 24 will be similarly confined vertically in its transit through region 62 from the right side boundary of the scattering volume 22 to the entrance point of ridge waveguide 20. The only section where the beam 24 is unconfined vertically is in its transit through the scattering volume 22 itself. Here the beam will begin to diverge vertically. Refraction and reflection at the dielectric interface can be ignored, as shown below.

The amount of divergence in the horizontal and vertical directions can be estimated using Gaussian beam propagation theory. If the beam intensity profile is separable into rectangular (x, y) coordinates, the propagation is resolved into two components representing beam propagation in the x and y directions. For a beam characterized by a beam waist, $\omega_0$, in the x- (or y-) direction, after propagating a distance, z the beam radius, $\omega_1$, in the x- (or y-) direction is given by $$\omega_1 = \omega_0[1+(z/z_R)^2]^{1/2}$$

where $Z_R = \pi\omega_0^2/\lambda$, is the Rayleigh length for the x- (or y-) direction. The wavelength in this expression is the wavelength in the dielectric, so $\lambda = 0.5\ \mu m/1.47 = 0.34\ \mu m$ in all sections of the waveguide.

The increase in beam width in the vertical direction as it traverses the scattering volume is $$2\omega_1 = 2 \times 1.01 \times \omega_0 = 1.01\ \mu m$$

where $\omega_0 = 0.5\ \mu m$, ($2\omega_0$=beam height=core height=$2a$)

$\lambda = 0.34\ \mu m$, effective wavelength and $z = 0.5\ \mu m$ (scattering volume width)

so that the beam width increases by 1%, a negligible amount. The phase front of the wave is still close to planar, so there will be negligible reflection or refraction at the silica interface in the scattering volume.

The beam is unconfined horizontally during propagation from the exit at ridge waveguide segment 18 to the re-entry point at ridge waveguide segment 20. When the beam is unconfined in one dimension only, solution of the Gaussian beam wave equation shows the beam radius, after propagating a distance z from the waist location, is given by $$\omega_1 = \omega_0[1+(z/z_R)^2]^{1/4}$$

where $Z_R = \pi\omega_0^2/\lambda$, is the same expression as before. The increase in beam width is $$2\omega_1 = 2 \times 1.21 \times \omega_0 = 1.21\ \mu m$$

so that the beam width has increased by 21% by the time it reaches the re-entry point at ridge waveguide segment 20. The beam can be efficiently coupled back into the ridge waveguide 20 if the waveguide is made 21% wider at this entrance point and gradually tapered back down to a width of 1 $\mu$m. This is illustrated by dotted lines 64 in FIG. 4.

(d) Beam Reflection at Interfaces

High reflection at interfaces could result in failure to deliver sufficient energy to the scattering volume 22 or could create standing wave fields in the scattering volume resulting in non-uniform spatial excitation of fluorophores. The reflection coefficient, r, at an interface with index of fraction $n_1$ at the incident side and $n_2$ on the transmission side of the interface, for normal incidence is $$R = (n_2-n_1)^2/(n_2+n_1)^2$$

For the ridge waveguide exit and re-entry interfaces, the effective refractive indices have been calculated above:

$n_2 = N_{slab} = 1.485$ $n_1 = N_{ridge} = 1.468$

The energy reflected is $R = 0.0068$ and is negligible.

For the slab waveguide/scattering volume interfaces, the effective refractive indices are:

$n_2 = N$ slab$=1.485$ $n_1 = N$ water$=1.333$

The energy reflected is $R = 0.0029$ and is again negligible.

Finally, exit from (and entrance to) the waveguide structure to free space effective refractive indices are:

$n_1 \sim 1.47$ $n_2 = 1.00$ hence $R = 0.0036$.

Thus, standing wave effects are not expected and reflection losses are sufficiently low to allow efficient delivery of laser energy to the scattering volume. In a preferred form of the invention, the laser beam 24 is produced by a continuous wave (C.W.) excitation source such as an Ar$^+$ion laser with a TEM$_{00}$ output. A modelocked laser source with a TEM$_{00}$ mode output could also be employed, although at higher cost. Fluorescent dyes typically have fluorescent lifetimes, $t_f$, of a few nanoseconds and absorption cross-sections of $10^{-16}$ cm$^2$, giving saturation intensities of $10^5$ to $10^6$ W/cm$^2$. Hence the maximum laser power in the waveguide for a 1 $\mu$m×1 $\mu$m waveguide is $$P = 10^6 \times 10^{-4} \times 10^{-4} = 10\ mW$$

so that a 4 W Ar$^+$ion laser is adequate.

It has been found that beam propagation through the waveguide structure described above can be accomplished with good spatial confinement of beam power in all sections of the structure. No undesirable standing wave pattern were produced in the scattering volume due to Fabry-Perot effects in the propagation direction or modal patterns with nodes in the transverse direction. Due to the incomplete confinement of the beam in the vertical direction the laser intensity at the very top and bottom of the scattering volume was high, and a uniform intensity irradiation of all fluorophores in the scattering volume was attained. Thus, the technique of using a waveguide to deliver the laser energy to the scattering volume offers well-defined confinement with precise alignment, with stray laser light scattering being minimized. Guided wave delivery is naturally suited for femtoliter size scattering volumes.

Figure 6:
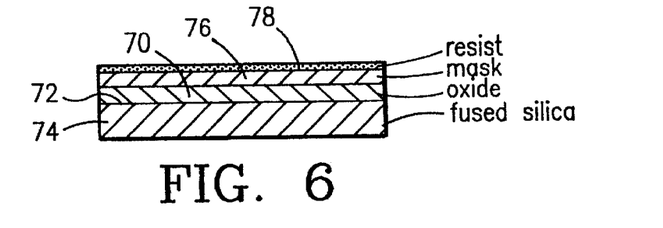
FIGS. 6 through 10 illustrate method steps for fabricating a microcapillary/optical waveguide device such as that illustrated in FIG. 4.

The above-described method of fabricating the microcapillary/waveguide device of the present invention is illustrated in FIGS. 6–10, to which reference is now made. As illustrated in FIG. 6, a coating, or film 70 of doped silica or related compound is deposited, as by a conventional a PECVD (plasma enhanced chemical vapor deposition) process, onto the top surface 72 of a substrate 74 of a material such as fused quartz (silica glass).

Figure 11:
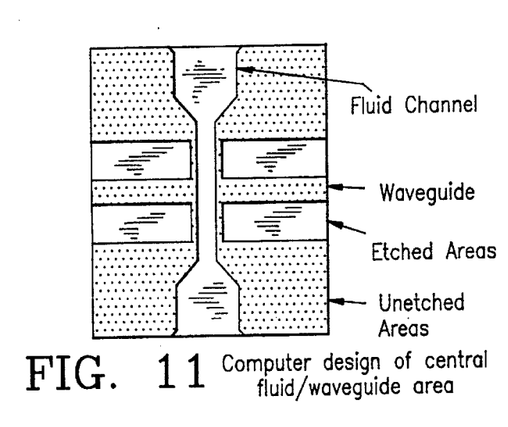
FIG. 11 illustrates a typical photolithographic pattern for use in fabricating the device of FIGS. 2 through 5.

A mask layer 76, which may be an aluminum film, is deposited on the top surface of layer 72 and a resist layer 78 is placed on top of the mask layer. Thereafter, the resist layer is photolithographically patterned by a suitable pattern such as that illustrated at 79 in FIG. 11, and the pattern in the resist layer is transferred to the metal mask layer 76 in conventional manner, as by an electron cyclotron resonance plasma etcher.

Figure 7:
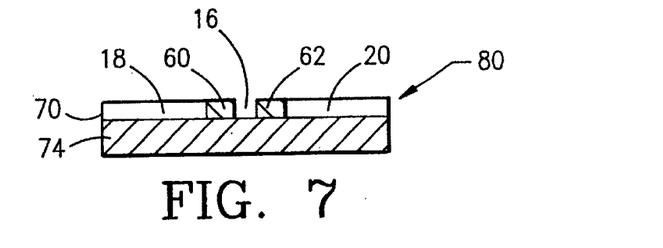

As illustrated in FIG. 7, the pattern in mask 76 is transferred to the silicon dioxide layer 72 by Reactive Ion Etching (RIE) in a $CF_4/O_2$ plasma, and the mask layer 76 is then removed by immersing the sample for 2–3 hours in, for example, a sulphuric acid and hydrogen peroxide etching solution. The resulting sample 80 illustrated in FIG. 7 includes the waveguide and microchannel pattern described above, with the cross section of FIG. 7 being taken along line 7—7 of FIG. 4, to illustrate the ridge waveguide segments 18 and 20 in side elevation and the regions 60 and 62 in cross section.

Figure 8:
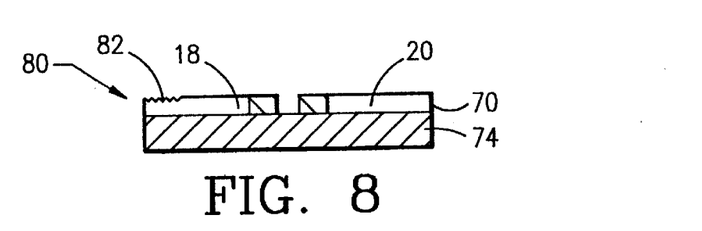
Figure 9:
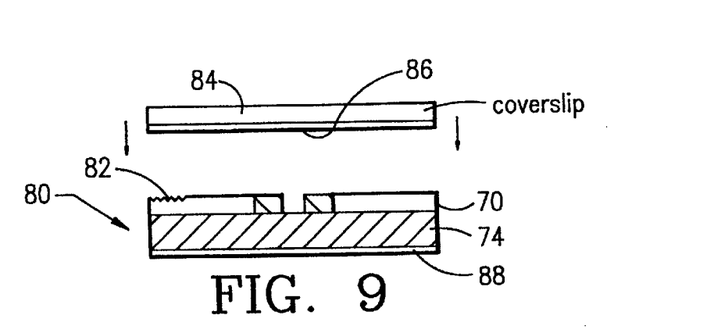
Figure 10:
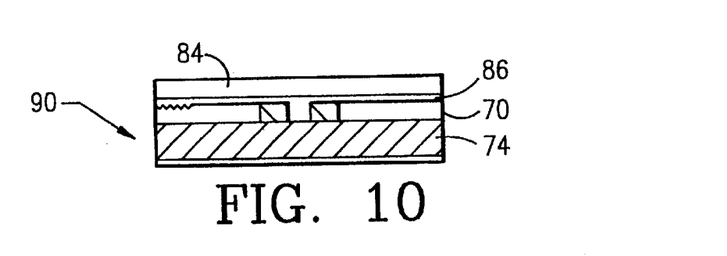

Following the patterning of the microchannel and waveguides, a second photolithographic patterning step is used to form an optical grating 82 having line widths of about 0.5 µm on a portion of the top surface of ridge waveguide segment 18, as previously described, using electron beam lithography. Thereafter, as illustrated in FIG. 9, a top cover plate such as a microscope coverslip 84 covered with a PDMS bonding layer 86 is sealed onto the top surface of the oxide layer 70. As a final fabrication step, an opaque layer 88 is deposited on the back of the sample, on the bottom of substrate 74, to eliminate fluorescence from the sample holder. FIG. 10 illustrates the completed microchannel/waveguide device 90 constructed in accordance with the foregoing steps.

Figure 12:
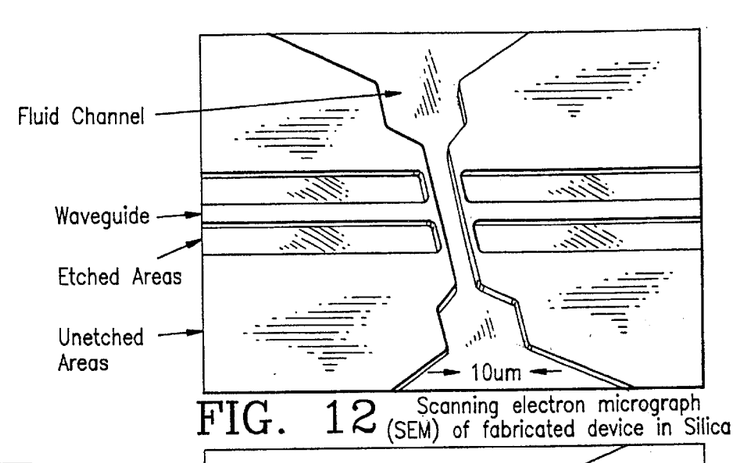
FIG. 12 is a scanning electron micrograph image of the device of FIG. 4 fabricated in silica.
Figure 13:
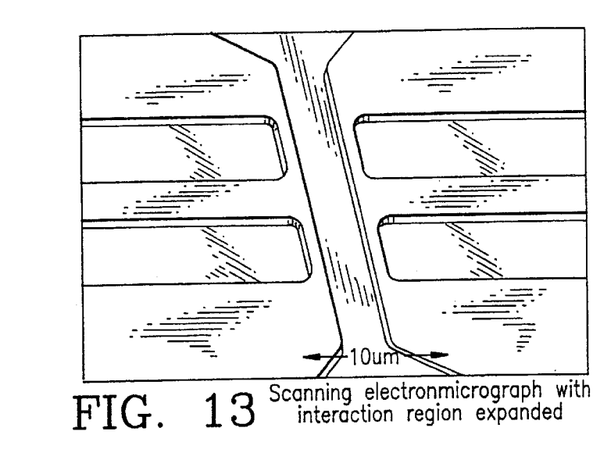
FIG. 13 is a scanning electron micrograph of the interaction region of the device of FIG. 4.
Figure 14:
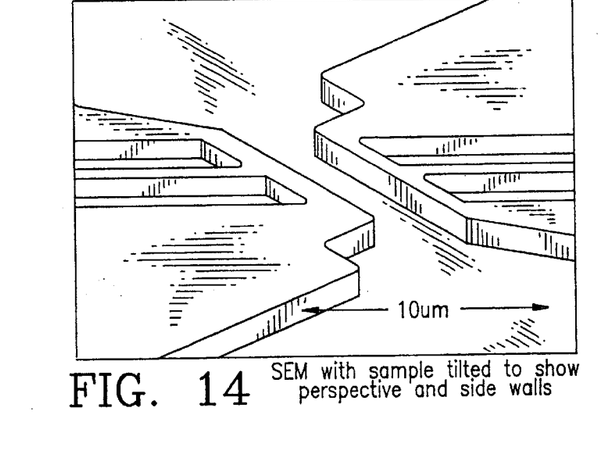
FIG. 14 is a scanning electron micrograph of the device of FIG. 4 with the device tilted to illustrate in perspective the sidewalls of the waveguides and microchannel.
Figure 15:
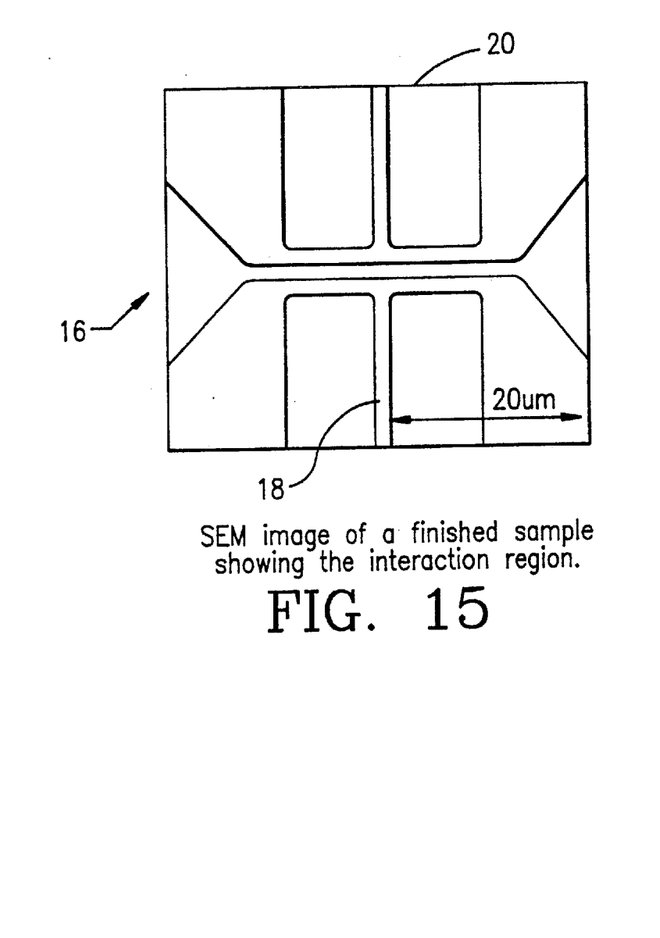
FIG. 15 is a scanning electron micrograph of a top plan view of a finished sample showing the interaction region.
Figure 16:
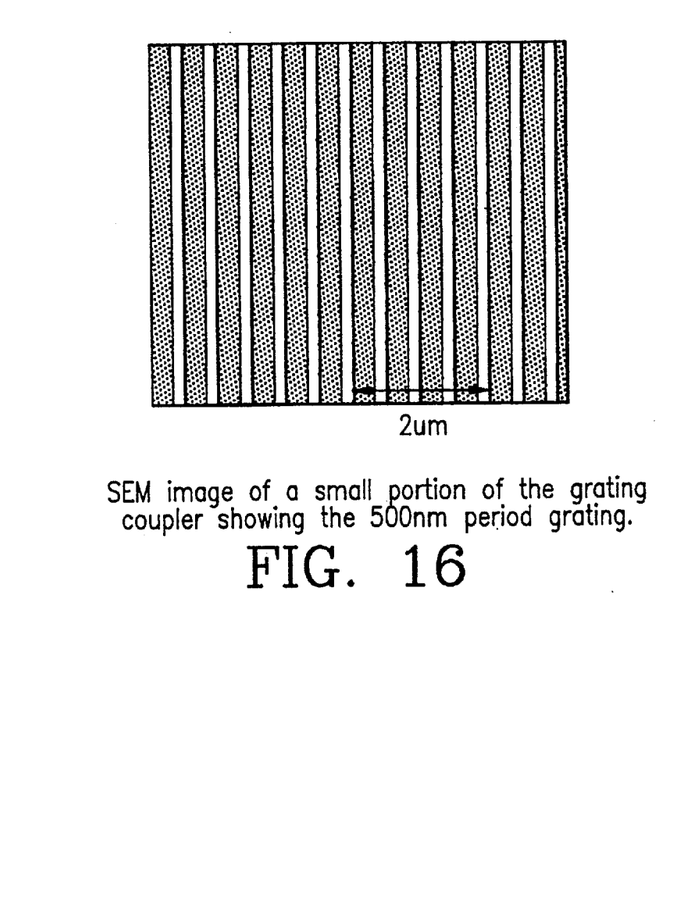
FIG. 16 is a scanning electron micrograph of a small portion of the grating coupler used on the waveguide of the device of FIG. 4, showing a 500 nm period grating.

FIGS. 12, 13 and 14 are scanning electron micrographs of the sample 80 fabricated in accordance with the foregoing process, before application of the coverslip 84. The SEM of FIG. 13 is an expanded view of the interaction region of the device of FIG. 12, while FIG. 14 is an SEM taken at a greater angle to show the device in perspective view. FIG. 15 is an SEM image of a finished sample in top plan view, showing the interaction region 22 discussed above. FIG. 16 is an SEM image of a small portion of the coupler grating 82, described with respect to FIG. 9. In the illustrated embodiment, the coupler grating has a period of 500 nm.

Figures 17, 18, 19, 20:
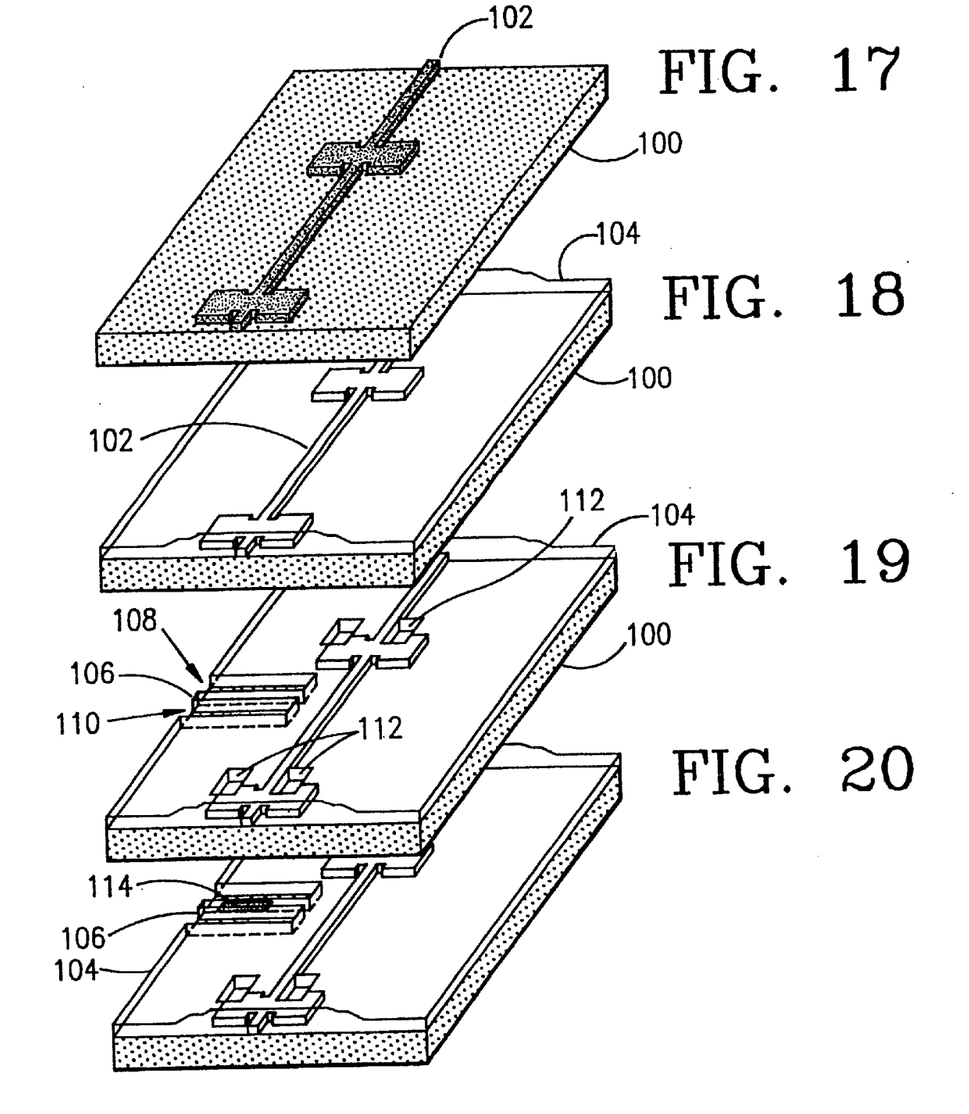
FIGS. 17 through 23 illustrate the method steps of a second fabrication process for the microcapillary/optical waveguide device of the present invention.

An alternative, and preferred, fabrication process for the microchannel/optical waveguide device of the present invention is illustrated in FIGS. 17 through 23, to which reference is now made. In this process, a glass substrate 100, which may be fused quartz, receives on its upper surface a sacrificial layer 102 which is shaped to define the microchannel structure which is to be provided on the substrate. The sacrificial layer 102 is deposited on the substrate 100 in the shape and dimensions of the desired capillary. As illustrated in FIG. 18, a high refractive index material 104, such as doped silicon dioxide is then deposited on the top surface of the substrate 100 and covers the sacrificial layer 102.

Thereafter, as illustrated in FIG. 19, conventional lithographic and etching processes, as described above, are used to form a ridge waveguide 106 in the layer 104 by etching channels 108 and 110 on opposite side of the waveguides. At the same time, irrigation holes 112 are formed through the layer 104 to expose the sacrificial layer at locations selected to permit removal of the sacrificial layer in a later step. Thereafter, as illustrated in FIG. 20, a diffraction-based optical coupler such as a grating is fabricated on the top surface of ridge waveguide 106 by lithographic patterning and electron beam etching.

Figures 21, 22:
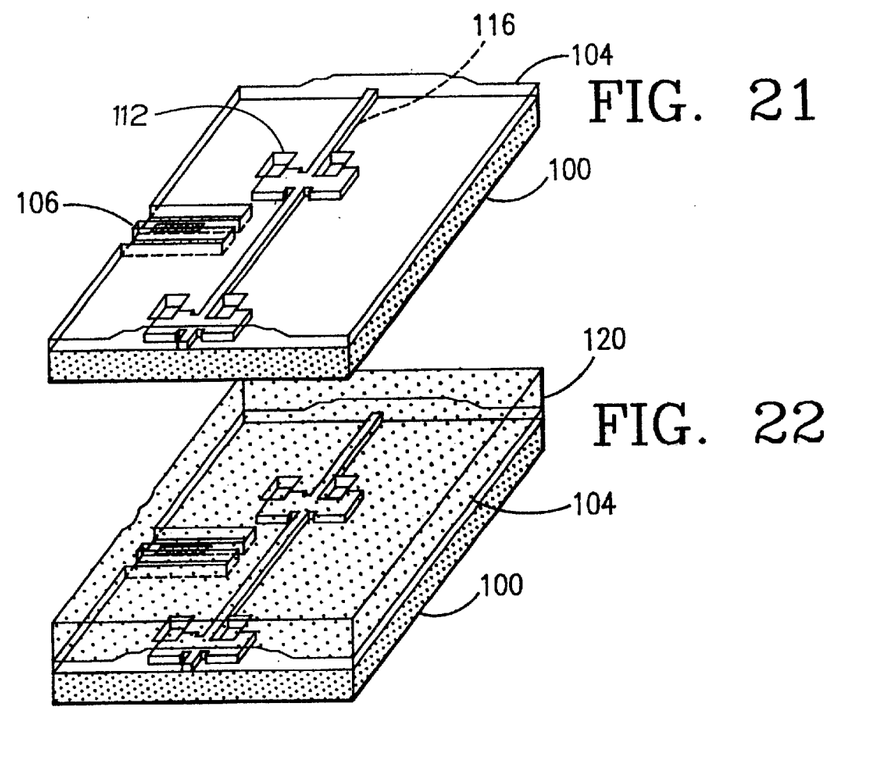
Figure 23:
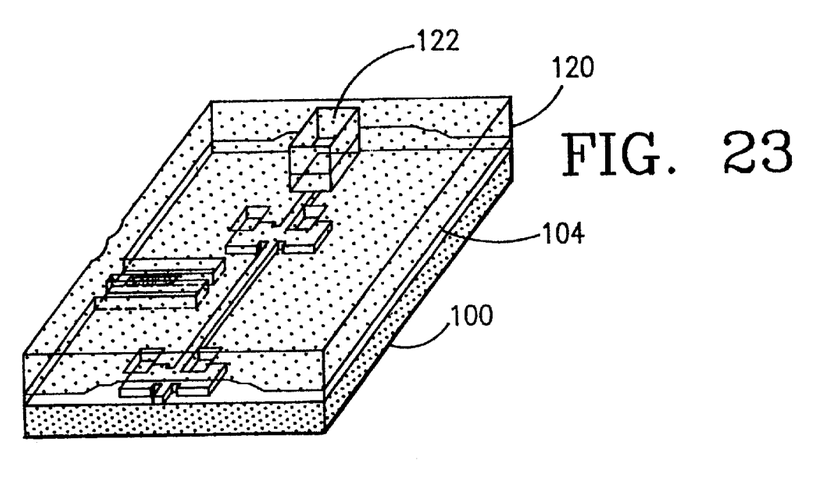
Figure 24:
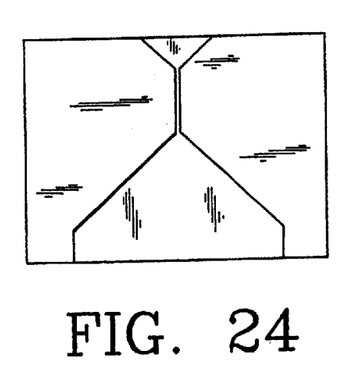
FIGS. 24 through 27 illustrate variations of the microcapillary configuration.
Figure 25:
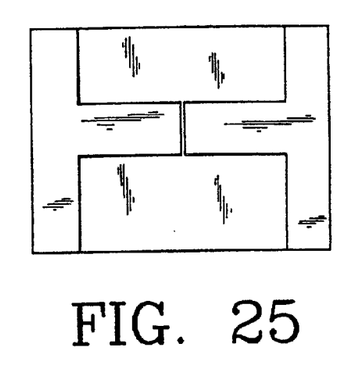
Figure 26:
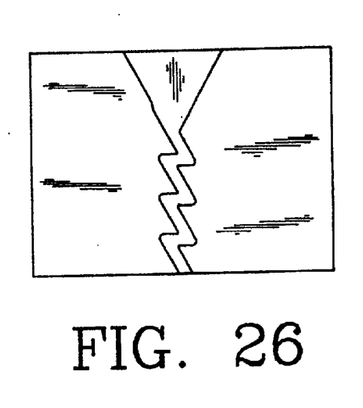
Figure 27:
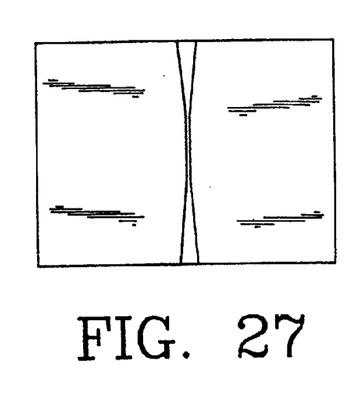

As illustrated in FIG. 21, the sacrificial layer 102 is next removed from the sample using wet chemistry supplied through the irrigation holes 112, forming a microchannel, or microcapillary 116 through the layer 104. Thereafter, as illustrated in FIG. 22, the irrigation holes are covered and the channels 108 and 110 are filled by depositing a material 120 having a low index of refraction. In the final step, illustrated in FIG. 23, access wells such as the well 122 are etched through the material 120 to contact the microcapillary 116 and to provide access to it. The device is then ready for use.

It will be understood that the shapes illustrated for the microchannels in the foregoing descriptions of fabrication processes are merely examples of the various shapes that can be provided. The photolithographic processes and the sacrificial layer process may be used to produce channels of any desired configuration. For example, FIGS. 24 through 27 are SEM images of 4 different microchannel configurations formed by the photolithographic process described with respect to FIGS. 6 through 10, and additional shapes may be provided to meet particular needs.

It will also be understood that the optical grating patterned on the top surface of the ridge waveguide, is illustrated in FIGS. 9 and 20, are patterned by the use of electron beam lithography in a resist layer and after the resist is developed the pattern is etched to a depth of approximately 100 nanometers to provide a grating which permits coupling of the laser beam 24 into the ridge waveguide segment 18, for example. Alternatively, it may desired to couple the beam into the waveguide at the input end 18a of waveguide segment 18. However, due to the presence of defects in the waveguide layer 14 (70 in FIGS. 6–10) it may be necessary to expand the beam coupling region to a width of, for example, 100 micrometers. This waveguide would then be tapered inwardly as it approaches the interaction region number with the capillary, with the rate of narrowing being slow enough to convert the energy of the beam 24 from the fundamental mode of the wide waveguide to the fundamental mode of the narrow waveguide.

The optical detection system for the present invention generally indicated at 54, 55 of FIG. 3, can be considered as being composed of collection optics 54, and spectral analysis components, detectors and signal processing electronics generally indicated at 55. Two detection systems are required: a high resolution one for spectral evaluation of the capillary-waveguide system, and one with a much larger spectral bandwidth for single molecule detection. Preferably, the same collection optics and detectors are used for both systems and only the spectral analysis components are changed.

Figures 28, 29:
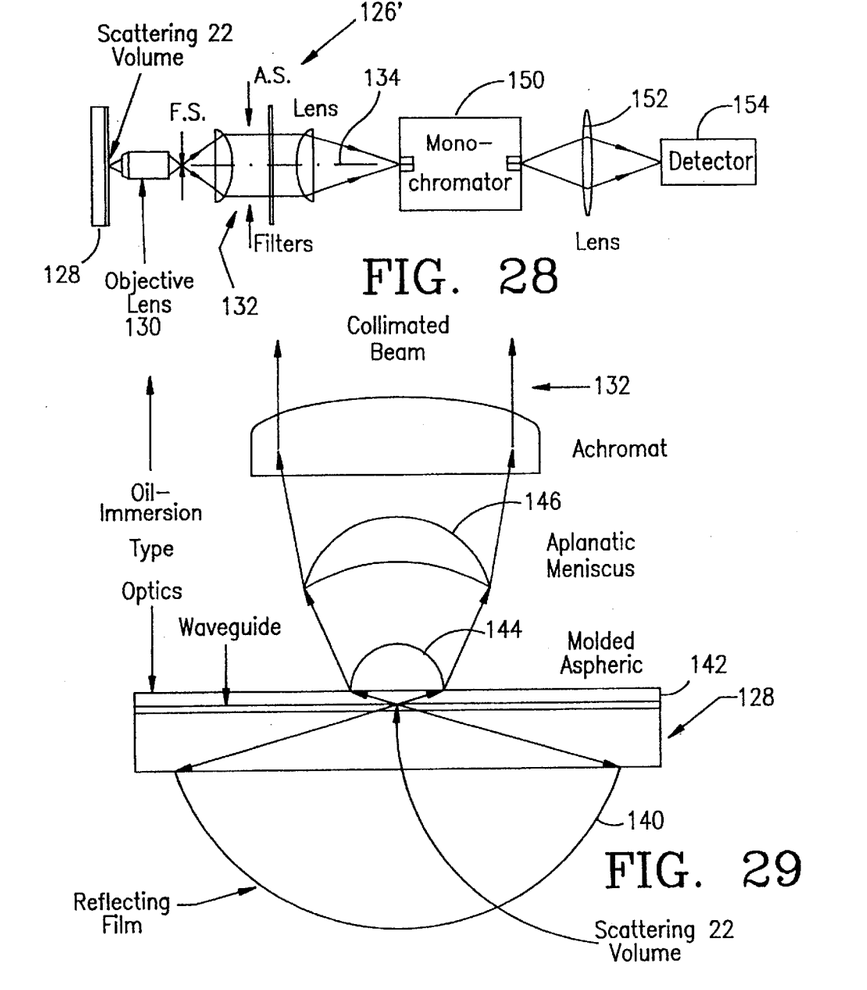
FIG. 28 is a schematic diagram of an optical detection system for use in spectral measurements for evaluating the performance of the device of the invention.
FIG. 29 is a diagrammatic illustration of a modified form of collection optics integrated into device of the invention to achieve improved collection angles.

In a preferred embodiment, collection optics 126 for capturing light emitted from the scattering volume 22 of an integral microchannel/optical wave device 128 may, for example, consist of a 0.8 NA microscope objective 130 and collimating optics 132 as shown in FIG. 28. The optical throughput or étendue, u, of the detection system is given by $$u = A\Omega$$
$$= 2.5 \times 10^{-10} m^2 sr$$

where

A is the imaged area of the scattering volume 22 transverse to the optical axis 134 of the detection system, $\Omega = 2\pi(1-\cos\theta) = 2.51$ sr., is the solid collection angle, $\theta = 53.1°$, the half collection angle and N.A.=n sin θ=0.8

In an initial design A=10 µm×10 µm; however, smaller waveguide-capillary structures with A≈1 µm×0.5 µm are preferred. The use of a microscope objective is a convenient, cost-effective method of achieving reasonable collection angles.

The geometrical collection efficiency is only 20% (0.2×4π sr) and the present waveguide structure is capable of accommodating integrated optics to achieve up to 80% efficiency.

Significant gains in geometrical light collection efficiency can be obtained by incorporating both refractive and reflecting collection optics into the microchannel/waveguide structure. As shown in FIG. 29 (not to scale) a spherical reflecting surface of diameter~10 mm formed by a coated glass hemisphere 140 returns rays emitted from the scattering volume 22 back to the scattering volume to double the number of photons traveling towards the refractive collection optics. The refractive optics function in the same manner as an oil-immersion microscope objective but instead of oil, a glass interposing medium such as a cover plate 142, to which a first lens 144 is optically contacted, is provided. This lens 144 is a molded aspheric of diameter~1 mm and can collect light with angles of incidence of up to ±79° (the same range as the spherical reflector). An aplanatic meniscus lens 146 and the other following lenses generally indicated at 132 are a mechanically separate set. This results in ease of alignment since the objective lens is always aligned to the tiny scattering volume. The amount of light collected by this system is 10.05 sterradians or 80%×4π sr.

Figure 30:
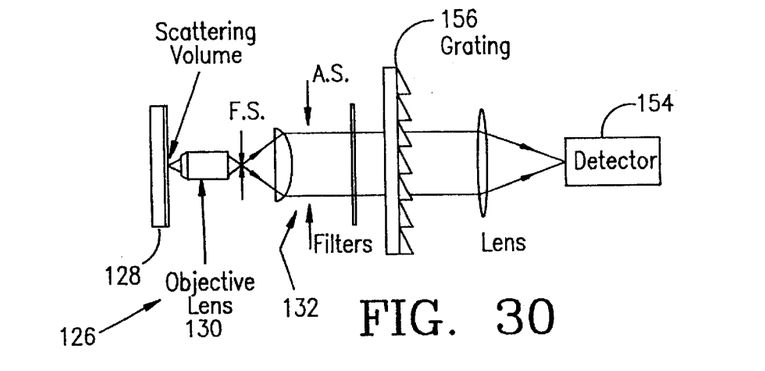
FIG. 30 is a schematic view of an optical system for multi-color fluorophor detection of very small numbers of molecules, including single molecule detection.

As noted above, the detection systems have two purposes. Firstly, to evaluate spectrally the performance of the waveguide and characteristics of the fluid flowing through the scattering volume, and secondly, to observe low light level or single molecule detection from fluorophores. The detection systems differ in the spectral components employed. For the first task, high resolution is required, while in the second case a broad (typ.~20 nm) emission is being sought. FIG. 28 illustrates the optical system described above as directing detected light to a monochromator 150, and through lens 152 to a detector 154 for making spectral measurements for evaluating the performance of the capillary/waveguide device 128. FIG. 30 illustrates the provision of a grating 156 in the collimating lens assembly 132, with light from assembly 132 being directed to detector 154. This assembly provides multicolor fluorophor detection of very small numbers of molecules, including single molecule detection.

Since étendue is conserved in an optical system (neglecting transmission losses) the above etendue can be used to calculate the maximum resolution achievable by any spectrally resolving components in the system. For a grating monochromator the étendue-resolution product is a given by $$uR = \beta S$$

where

S=area of the grating=0.1 m×0.1 m
β=slit height/focal length=h/f
u=2.5×10$^{-10}$ m$^2$sr, as before for A=10 μm×10 μm Using the f=0.5 m ISA Instruments monochromator with slit height, h=89 μm (=slit width) the maximum achievable resolution, R and minimum resolvable bandwidth, δλ in the visible region (at 500 nm) is $$R = 71{,}000 \text{ or } \delta\lambda = 70 \text{ pm}$$

It is important to achieve etendue-limited performance as this ensures that the maximum amount of light reaches the detector for a given resolution. If higher resolution is required, then the optical throughput is proportionately reduced unless an instrument with a higher étendue-resolution product is used. For the detection of fluorescent bands in a multi-color system the small grating 156 replaces the monochromator. In this case a minimum resolvable bandwidth of ~5 nm is required and the grating size is correspondingly larger. A 4-color dye system consisting of Applied Biosystems dyes: FAM (521 nm), HEX (556 nm), TAMRA (580), ROX (605 nm) may be used in the present system, for example.

There are at least two preferred detectors for single molecule detection. SPAD's or single photon avalanche photodiodes (EE&G SPCM-200) have high quantum efficiencies (up to 60%) but suffer from saturation at higher light levels. Photomultiplier tubes have lower quantum efficiencies (up to 20%) but can be operated at lower gain and are hence more versatile. The higher efficiency of the SPAD offers an advantage in the signal to noise ratio which must be obtained for single molecule detection. A general purpose, but fast, sensitive PMT (Hamamatsu R1387) may be used at higher light levels. A fast (risetime~1.5 ns) low-noise pre-amplifier is required for both detectors. At moderate and high light levels, conventional synchronous detection with a chopped laser beam and a lock-in amplifier may be employed. At single photon light levels, gated photon counting techniques are required where the number of photons within a given gate period are detected and counted. When a c.w. source is used, the exact time of occurrence of the photon burst due to a single molecule excitation is unknown. Assume the following:

t=duration of photon burst=1 ms n=number of detected photons in burst=10$^4$ to 10$^6$ and that the interval between photon bursts is approximately 20 ms. About 2,000 counts may be observed over a 20 ms interval, where each count represents the detected photons in consecutive gated time intervals of 10 μs duration. A photon burst, if present, will occupy about 100 counts and can be extracted by autocorrelation or other techniques from the data record. A multichannel scaler with discriminator is required for this technique.

At light levels intermediate between the foregoing extremes, synchronous photon counting can be used. This is a variation on conventional synchronous detection where instead of a lock-in, two counters count photons during the open and closed portions of the chopper cycle using the output from a single detector. A multichannel scaler but without a discriminator is required for this technique.

Performance of the flow channel was assessed by supplying lambda phage DNA solution to the channel. It was found that surface forces in the channel were sufficient to fully fill the structure, and for test purposes fluorescence was observed using an epi-illumination ZEISS microscope equipped with a complete set of fluorescence filters. A CCD camera was used to take pictures of single molecules of DNA flowing through the channels. Two small reservoirs of DNA solution were kept in contact with the samples and the DNA was driven through the structure electrophoretically. Voltages on the order of a few volts were brought to the solution by copper wires and since the conductivity of the solution was large, the majority of the voltage drop occurred across the samples.

Accurate determination of the flow velocity of the molecule being examined in the narrow region near the scattering volume was accomplished by fabricating waveguides at 2 points along the channel and using LIP to measure flow velocity between the points. The CCD camera was used as the detector to image the 2 interaction volumes simultaneously and when a fluorescent dye was introduced into the flow the delayed time between the first detection of fluorescence at the 2 sites permitted accurate average flow velocity measurements. It was found that the narrow height of the channels created a self-filtering effect which prevented dust particles from entering the narrow portion of the microchannels. Thus, the flow of DNA molecules was observed for extended periods.

Figure 31:
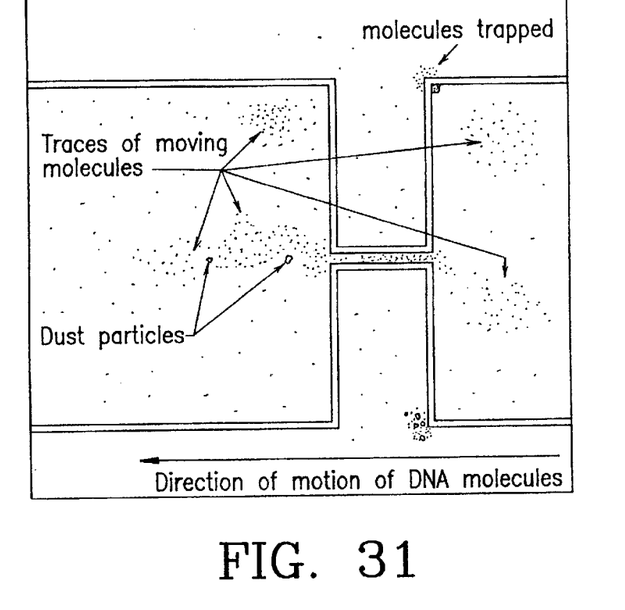
FIG. 31 is a photomicrograph of DNA molecules flowing through a 1 micrometer wide microchannel.
Figure 32:
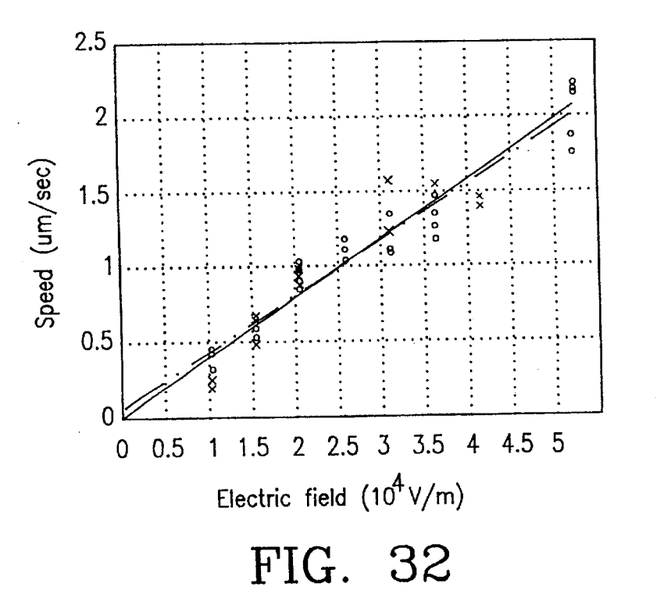
FIG. 32 is a graph of flow speed versus applied electric field.

As illustrated in the photomicrograph image of FIG. 31, the molecules of DNA were seen to follow electric field lines in the microchannel. Since the microcapillaries being tested were 30 micrometers long, the electric field inside the channel reached intensities as high as $5 \times 10^4$ volt per meter as shown in the graph in FIG. 32. This voltage strongly accelerated the DNA inside the capillary and led to shearing of the DNA molecules in some cases. The photomicrograph of FIG. 31 was made with an exposure time of 30 seconds. The intensity of light inside the channel is proportional to the local time-average density of the DNA. The fact that the intensity is not constant indicates that the DNA are accelerated by the electric field; accordingly, the density is inversely proportional to the speed of the DNA. As illustrated, the density is high at the beginning of the channels and decreases as the DNA gains in speed.

A significant difficulty in the measurement of DNA molecules by induced fluorescence is the photo-destruction of dye molecules. If the excitation-emission cycle is, for example, 5 ns long, the required observation time is $t$=10 ms to 1 s For a 10 micrometer long scattering region, flow velocities of 1 mm per s to 10 micrometers per s are required. However, in accordance with the present invention, by decreasing the scattering volume, the effective number density of fluorophores is increased proportionately for a consequent improvement in the signal to noise ratio. A sufficient laser intensity is then available to excite the fluorophore to near saturation point to achieve a maximal fluorescence rate. The observation of fluorescence is observed over the entire photo-lifetime of the molecule, and all molecules passing through the capillary are excited. The full channel width is imaged, collecting photons from all molecules passing through the capillary, with laser power requirements being much smaller when the scattering volume is considerably reduced in size.

Accordingly, an integrated fluid channel and waveguide system has been provided which relies on simultaneously microfabricating channels for the flow of fluids and an optical waveguide for providing illumination for the channel on a single substrate, or chip. The advantage of the waveguide compared to standard illumination is that it provides a well-defined, small interaction region which results in a lower probability of having more than one molecule in the interaction volume and results in a decrease in background noise. Moreover, the small portion of the structure which is subjected to the excitation light reduces the scattered light, and these properties lead to an increase in the efficiency of the detection process. Although the invention is described in terms of the detection of DNA molecules, similar structures can also be used to study the motion of polymer strands in restricted channels, for example, as well as for other purposes. Thus, although the invention has been described in terms of preferred embodiments, it will be understood that numerous modifications and variations may be made without departing from the true spirit and scope thereof, as set forth in the following claims.

What is claimed is:

1. Apparatus comprising:
    at least one microchannel for conveying material;
    at least one optical waveguide formed monolithically with said microchannel for propagating light for interaction with said material in an interaction region within said microchannel.

2. The apparatus of claim 1, wherein said waveguide is a ridge waveguide having a core, and further including:
    a channel on each side of said core to form core side walls, a cover engaging a top wall of said core, and a bottom wall of said core engaging said substrate, to provide a cladding for said core whereby a laser beam directed into said waveguide will propagate along the waveguide to said interaction region.

3. The apparatus of claim 2, wherein said microchannels and said waveguide are so dimensioned that said interaction region has a volume in the femtoliter range.

4. The apparatus of claim 3, further including means to direct a laser light beam into said waveguide for propagation along said waveguide to said interaction region.

5. The apparatus of claim 4, further including an optical sensor aligned with said interaction region.

6. The apparatus of claim 5, further including means for delivering material containing fluorophores to said interaction region in said microchannel for excitation by a laser light beam propagating along said waveguide.

7. The apparatus of claim 6, wherein said optical sensor includes means for detecting light emitted by said material in said interaction region.

8. The apparatus of claim 7, wherein said microchannel is dimensioned to pass a single molecule at a time through said interaction region.

9. The apparatus of claim 6, wherein said means for delivering material includes an enlarged inlet region in said microchannel.

10. The apparatus of claim 5, wherein said optical sensor is orthogonally related to said waveguide and said microchannels.

11. The apparatus of claim 5, wherein said at least one microchannel includes an enlarged inlet portion and an inner portion which tapers inwardly to said interaction region.

12. The apparatus of claim 4, wherein said means to direct includes an optical grating on said waveguide.

13. The apparatus of claim 4, wherein said means to direct includes an enlarged inlet to said waveguide.

14. The apparatus of claim 1, further including means to direct a beam of laser light into said waveguide for propagation along the waveguide and through said interaction region.

15. The apparatus of claim 14, wherein said means to direct includes an optical grating on said waveguide.

16. The apparatus of claim 14, wherein said means to direct includes an enlarged input end on said waveguide for receiving light.

17. The apparatus of claim 1, further including an optical sensor aligned with said interaction region.

18. The apparatus of claim 17, wherein said waveguide, said microchannel and said optical sensor are orthogonal.

19. The apparatus of claim 1, wherein said waveguide and said microchannel are so dimensioned that said interaction region has a volume in the femtoliter range.

20. The apparatus of claim 1, wherein said waveguide includes an inlet portion on a first side of said microchannel and an outlet portion on a second side of said microchannel, said inlet and outlet portions being aligned along an optical axis which intersects said microchannel at said interaction region.

21. The apparatus of claim 1, wherein said interaction region of said microchannel has a depth in the range of 0.5 μm.

22. The apparatus of claim 21, wherein said waveguide has an outlet adjacent said interaction region, said outlet having a minimum dimension of about 1.0 μm.

* * * * *